US00PP37756P2

(12) United States Plant Patent
Hung et al.

(10) Patent No.: US PP37,756 P2
(45) Date of Patent: Oct. 13, 2026

(54) ***HOMALOMENA* PLANT NAMED 'HUTAHM05'**

(50) Latin Name: *Homalomena occulta*
Varietal Denomination: HUTAHM05

(71) Applicant: Huta Green Company Limited, Hanoi (VN)

(72) Inventors: Pham Ngoc Hung, Hiep Cuong Commune (VN); Le Tuan Anh, Hanoi (VN)

(73) Assignee: Huta Green Company Limited, Hanoi (VN)

( * ) Notice: Subject to any disclaimer, the term of this patent is extended or adjusted under 35 U.S.C. 154(b) by 0 days.

(21) Appl. No.: 18/831,403

(22) Filed: Jan. 14, 2025

(51) Int. Cl.
*A01H 6/00* (2018.01)
*A01H 5/12* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ..... A01H 6/00; A01H 5/12
See application file for complete search history.

*Primary Examiner* — Keith O. Robinson
(74) *Attorney, Agent, or Firm* — Samuel R. McCoy, Jr.

(57) ABSTRACT

'HUTAHM05' is a new and distinctive *Homalomena* plant which is characterized by a compact, upright growth habit with conspicuously variegated foliage that is predominantly colored pale green-yellow, with dark green blotches, and a high degree of pale yellow-green and pale green flecking, mid-green petioles, and the stability of all characteristics from generation to generation. The new variety is typically produced as an indoor ornamental plant.

3 Drawing Sheets

Latin name of the genus and species: The Latin name of the genus and species of the novel variety disclosed herein is *Homalomena occulta.*

Variety denomination: The inventive variety of *Homalomena* disclosed herein has been given the variety denomination 'HUTAHM05'.

BACKGROUND OF THE INVENTION

Parentage: The claimed plant originated as a Ethyl methanesulfonate-induced, whole-plant mutation of an unnamed *Homalomena occulta* (not patented). In the spring of 2019, meristematic tissue culture propagation of said *Homalomena occulta* plant was initiated at a plant tissue culture laboratory in Hanoi, Vietnam. After five months in culture, the plant tissue was transferred to an agar medium to induce multiplication of meristematic plant tissue. After one month, the plant tissue was treated with Ethyl methane sulfonate in order to induce mutation. Once these plant tissue cultures developed juvenile leaf shoots and calluses, they were transferred to a soilless growing media and acclimatized in a greenhouse. This process resulted in approximately 5000 rooted young plants. Said plants were grown to the 4-leaf stage, at which point any plantlets exhibiting variation in leaf color, variation in leaf shape, or leaf variegation were isolated. In February of 2020, after evaluating said isolated plants, one plant was observed to exhibit unique foliage variegation relative to all other candidate plants resulting from the induced-mutation. The plant was isolated and further evaluated to confirm the characteristics first observed. In January of 2022, it was determined that the unique foliage variegation and coloration of the claimed plant would prove favorable for commercial marketability.

Asexual Reproduction: Asexual reproduction of 'HUTAHM05', by way of meristematic tissue culture propagation, was first performed in 2022 at a plant tissue culture laboratory in Hanoi, Vietnam. Three successive generations so produced have shown that the unique features of the instant cultivar are stable and reproduced true to type.

SUMMARY OF THE INVENTION

The cultivar 'HUTAHM05' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Homalomena* cultivar 'HUTAHM05'. These traits, in combination, distinguish 'HUTAHM05' as a new and distinct cultivar.

1. *Homalomena* 'HUTAHM05' exhibits a compact, upright growth habit; and
2. *Homalomena* 'HUTAHM05' exhibits variegated cordate foliage borne on green petioles; and
3. *Homalomena* 'HUTAHM05' exhibits conspicuously variegated foliage that is predominantly colored with pale green-yellow with dark green blotches and a high degree of pale yellow-green and pale green flecking.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
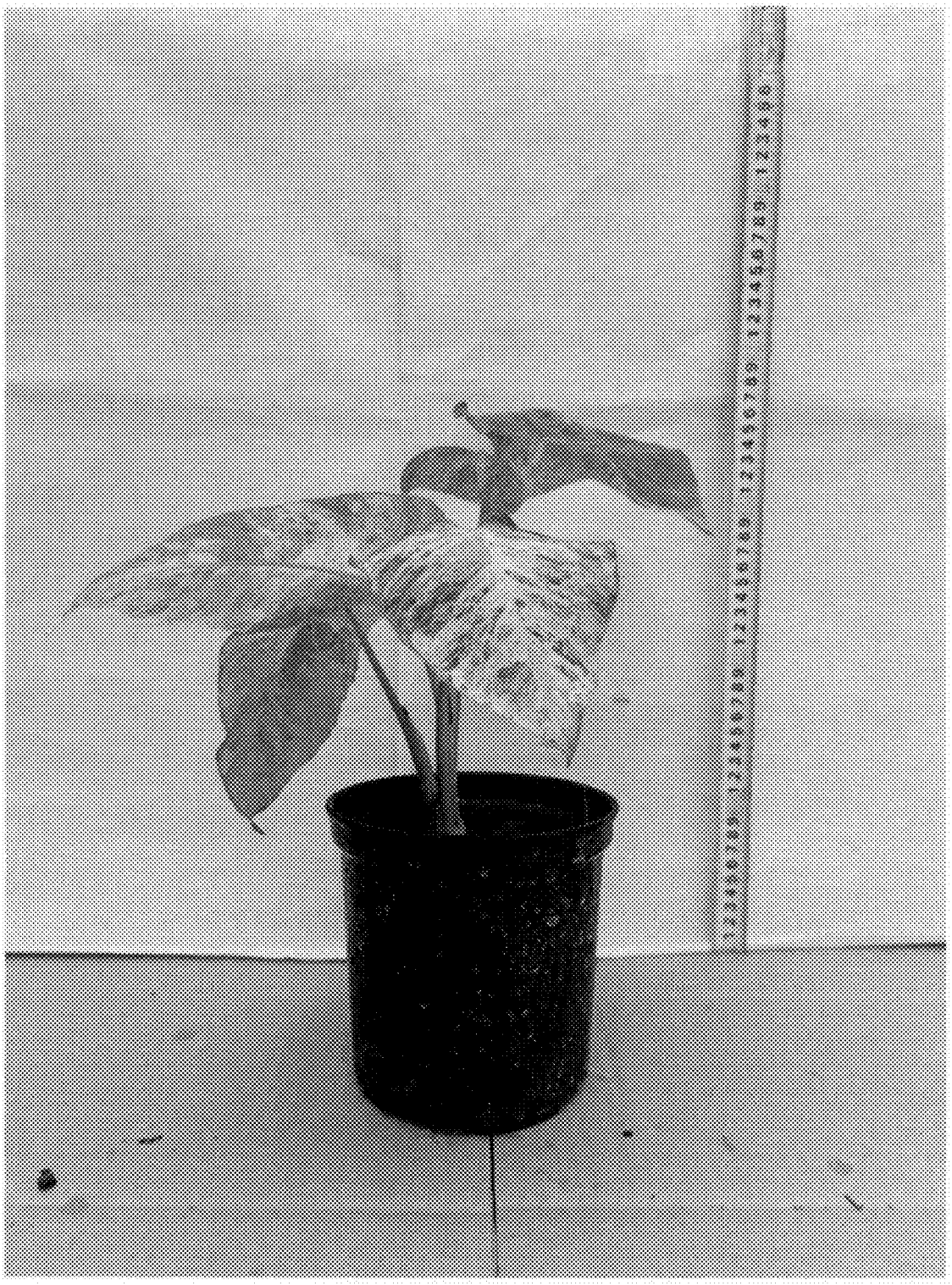
FIG. 1 illustrates an exemplary plant of the new cultivar, 'HUTAHM05', in profile. The plant shown is approximately 4 months old from a rooted cutting, potted into a 15 cm nursery container, grown in a greenhouse in Hanoi, Vietnam.
Figure 2:
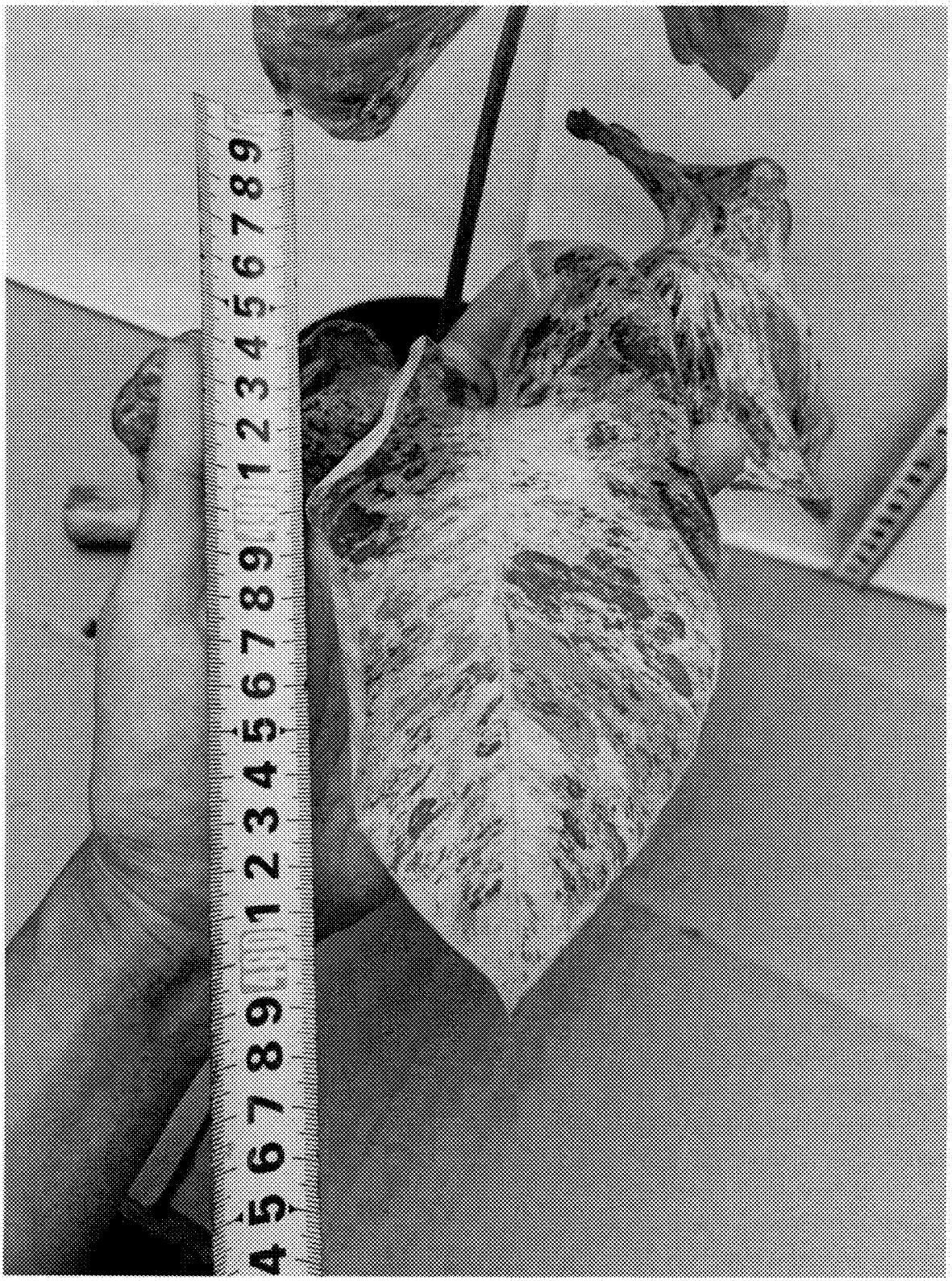
FIG. 2 illustrates the predominant color and variegation pattern of the mature foliage of 'HUTAHM05'.
Figure 3:
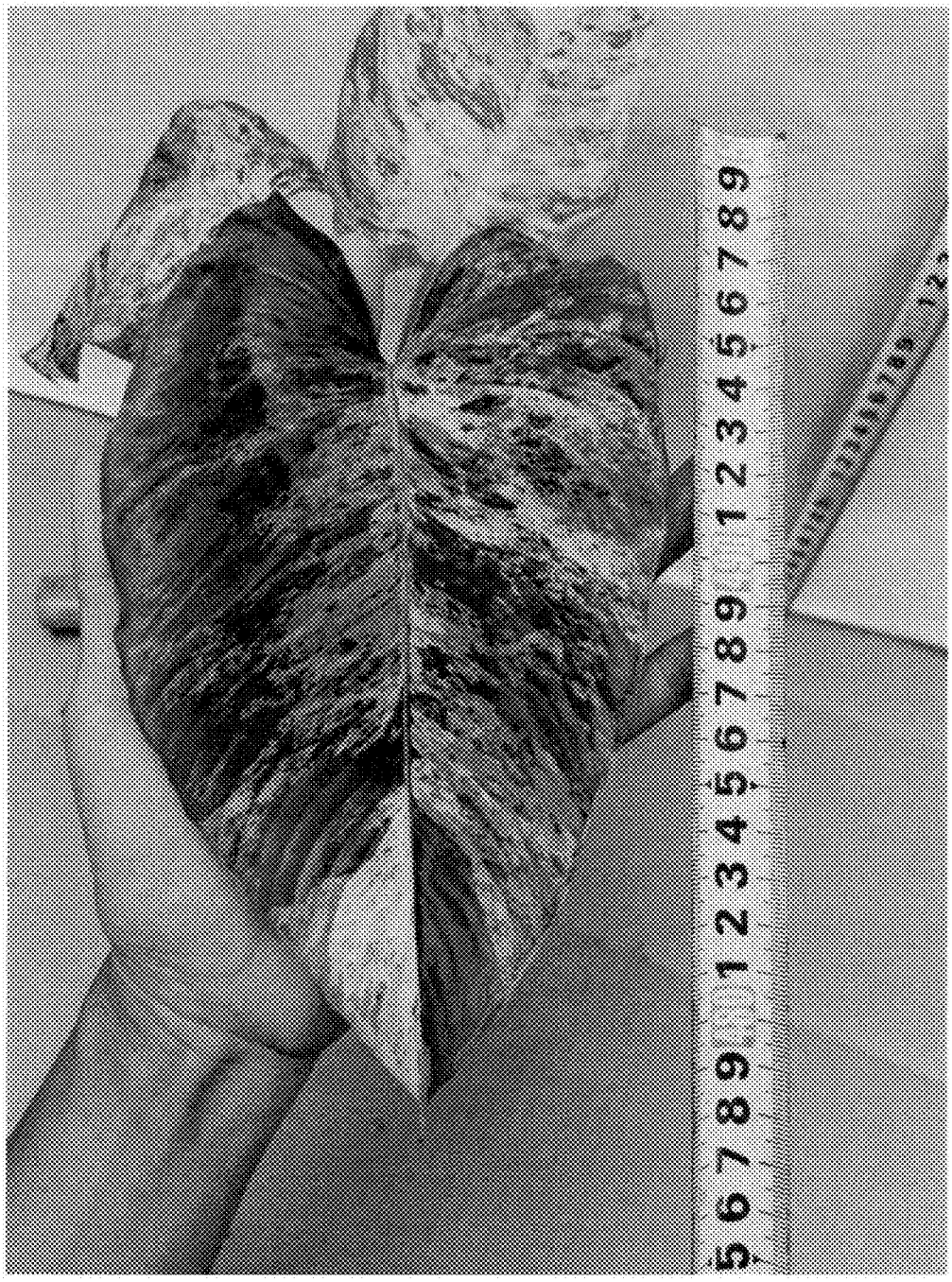
FIG. 3 illustrates additional variegation patterns of the mature foliage of 'HUTAHM05'.

The following observations and measurements made in October of 2023 describe a 4-month-old 'HUTAHM05' plant grown in a 15 cm nursery container at commercial greenhouse in Hanoi, Vietnam. Plants were produced using conventional greenhouse production protocols for *Homalomena* species which consisted of overhead irrigation twice a week, weekly applications of a liquid 20-20-20 fertilizer at an electroconductivity of 0.8, and anti-bacteria oxalinic acid at a rate of 375 parts-per-million and Imidacloprid insecticide at a rate of 100 parts-per-million applied every two weeks. Plants were grown under shade (ranging from 5,000 to 15,000 lux) with ambient temperatures ranging from 20 to 35 degrees Celsius and humidity levels ranging from 70 to 80 percent.

Those skilled in the art will appreciate that certain characteristics will vary with older or, conversely, with younger plants. 'HUTAHM05' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on The Royal Horticultural Society Colour Chart, The Royal Horticultural Society, London, Second Edition.

A botanical description of 'HUTAHM05' and comparisons with the parent and the most similar variety of common knowledge are provided below.

General plant description:

*Growth habit*.—Monopodial evergreen perennial, developing multiple shoots from rhizomes as plants age; individual shoots will develop an unbranched stem with age though none have been observed on the claimed plant.

*Plant profile*.—Upright, globular.

*Height*.—31 cm to the top of the floral plane.

*Width*.—36 cm.

*Plant vigor*.—Vigorous.

*Propagation*.—Method — Meristematic tissue culture. Time to initiate roots — Approximately 24 weeks to initiate roots at an average ambient temperature of 25 degrees Celsius. Crop time — Approximately 16 weeks to produce a well-rooted, marketable 20 cm container from a rooted cutting.

*Environmental tolerances*.—Moderately high tolerance to rain; low to moderate tolerance to wind; not drought tolerant; tolerant of temperatures to at least 35 degrees Celsius. Cold hardy to USDA Hardiness Zone 10.

*Disease and Pest Susceptibility or Resistance*.—'HUTAHM05' has distinguished itself as less susceptible to pests within the Tetranychidae and Aphididae families, as well as *Spodoptera litura* which are recognized as common pests to *Homalomena*. 'HUTAHM05' has not been observed to be resistant to pathogens common to the genus such as leaf rust diseases from the fungus *Puccinia paullula*.

Root system:

*General*.—Rhizomatous and bearing a freely-branching, moderately dense network of fleshy roots which are distributed from shallow to moderately deep within the soil profile.

Foliage:

*Arrangement*.—Alternate to spiraled.

*Division*.—Simple.

*Attachment*.—Petiolate.

*Quantity of leaves per shoot*.—4.

*Average quantity of shoots per plant*.—3.

*Quantity of leaves per plant*.—Approximately 4.

*Lamina*.—Shape — Cordate. Apex — Broadly acuminate. Base — Cordate. Aspect — Convex with the apex curling downward. Attitude — Outward to somewhat pendulous. Dimensions — 16.5 cm long and 11.25 cm wide, at the widest point. Margin — Entire; moderately, coarsely undulating. Texture and luster, adaxial surface — Smooth, glabrous, and slightly glossy. Texture and luster, abaxial surface — Smooth, glabrous, and matte. Juvenile and mature color, adaxial and abaxial surfaces — The variegation pattern and consequently the laminar coloration is variable from one leaf to the next. Some laminas are predominantly colored with a mixture of dark green and yellow-green with irregular pale green-yellow blotches and a high degree of pale yellow-green and pale green flecking, whereas the majority of laminas are predominantly pale green-yellow with dark green blotches and a high degree of pale yellow-green and pale green flecking. Regardless of the variegation pattern and the amount of each color present, the color recitations are the same. The dark green coloration is nearest to RHS 143B; the pale green-yellow coloration is nearest to a combination of RHS 2D and 4D; the pale yellow-green flecking is nearest to RHS 144D; and the pale green flecking is nearest to a combination of RHS 141B and 143B. Venation — Vein pattern — Pinnate. Vein color, adaxial surface — Midrib is green-yellow, RHS 2D, and streaked with yellow-green, RHS 144D. Lateral and tertiary veins are yellow-green, nearest to RHS 144D. Vein color, abaxial surface — The main and lateral veins are a mixture of greens, nearest to a combination of RHS 143B and 143C. Petiole — Attachment — Sheathed. Aspect — Terete. Length — Approximately 24.5 cm. Width — Approximately 1.5 cm, including the petiole wings, at the proximal end and 0.5 cm at the distal end. Strength — Moderately strong. Texture — Verrucose; glabrous. Luster — Matte to very slightly glossy. Color, adaxial and abaxial surfaces — Juvenile petioles are green, nearest to a combination of RHS 143B and 141C; mature petioles are green, nearest to RHS 143B, and distally suffused with greyed-yellow, nearest to a combination of RHS 161A and 162B. Petiole wings — General Description — Two petiole wings are present at the base of each petiole. Length — 10.5 cm on mature petioles. Width — 1.0 cm at the base on mature petioles. Margins — Entire; very light, coarse undulation. Texture and luster — Glabrous and very slightly glossy. Color, juvenile — Emerging yellow-green, nearest to RHS 144A, with broad green margins, RHS 143A; aging to yellow-green, RHS 145C, with moderate to heavy greyed-red suffusion, RHS 182B. Color, mature — Green, nearest to RHS 143B with a slighter lighter green closer to the point of attachment to the lamina, nearest to a combination of RHS 144D and 145C.

Inflorescence: No flowering has been observed to date.

Flower buds: No flowering has been observed to date.

Flowers: No flowering has been observed to date.

Reproductive organs: No flowering has been observed to date.

Seed and fruit: No flowering has been observed to date.

Comparisons with the parent: Plants of the new cultivar 'HUTAHM05' may be distinguished from the parent, an unnamed *Homalomena occulta* plant (not patented), by the characteristics described in Table 1.

TABLE 1

| Characteristic | 'HUTAHM05' | The parent. |
|---|---|---|
| Variegation pattern and general coloration of the foliage. | Variegated foliage that is predominantly colored pale green-yellow, with dark green blotches, and a high degree of pale yellow-green and pale green flecking. | Non-variegated; homogeneously dark green. |

Comparisons with the most similar commercial variety: Plants of the new cultivar 'HUTAHM05' may be distinguished from the most similar commercial comparator known to the inventor, *Homalomena rubescens* 'HUTAHM06' (U.S. Plant Pat. No. 36,050), by the characteristics described in Table 2.

TABLE 2

| Characteristic | 'HUTAHM05' | 'HUTAHM06' |
|---|---|---|
| Expression of the foliar color patterns; adaxial and abaxial surfaces. | Variegated foliage that is predominantly colored pale green-yellow, with dark green blotches, and a high degree of pale yellow-green and pale green flecking. | Varying from leaf to leaf with more laminas being nearly solid yellow-green with a small amount of dark green and greyed-green splotches, to others nearly solid yellow-green with large dark green and greyed-green blotches. |
| Mature petiole color. | Green, with a slighter lighter green suffusion towards the point of attachment to the lamina. | Dark greyed-red at the base, becoming lighter greyed-red with yellow-green suffusion towards the lamina. |

That which is claimed is:

1. A new and distinct variety of *Homalomena occulta* plant named 'HUTAHM05', substantially as described and illustrated herein.

* * * * *